United States Patent
August et al.

(10) Patent No.: US 7,229,798 B2
(45) Date of Patent: Jun. 12, 2007

(54) TRANSPOSON MEDIATED MULTIPLEX SEQUENCING

(75) Inventors: Paul R. August, Danville, NH (US); Pamela J. Keagle, Leominster, MA (US); Henry Long, Cambridge, MA (US); Anna Wiencis Montmayeur, Waltham, MA (US); Katherine Call, Malden, MA (US); Michael Draper, Plaitsow, NH (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 581 days.

(21) Appl. No.: 10/332,834

(22) PCT Filed: Jul. 5, 2001

(86) PCT No.: PCT/US01/21269

§ 371 (c)(1),
(2), (4) Date: May 5, 2003

(87) PCT Pub. No.: WO02/04674

PCT Pub. Date: Jan. 17, 2002

(65) Prior Publication Data

US 2003/0219779 A1 Nov. 27, 2003

Related U.S. Application Data

(60) Provisional application No. 60/216,381, filed on Jul. 7, 2000.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .................. 435/91.2; 435/6; 435/91.1; 536/23.1; 536/24.3; 536/24.33; 536/25.3; 536/25.32

(58) Field of Classification Search .............. 435/6, 435/91.1, 91.2, 183, 252.3, 320.1, 455; 436/94; 536/23.1, 24.3, 24.33, 25.3
See application file for complete search history.

(56) References Cited

FOREIGN PATENT DOCUMENTS

| WO | WO 97/46714 | 12/1997 |
|----|-------------|---------|
| WO | WO 98/37205 | 8/1998 |
| WO | WO 00/26243 | 5/2000 |

OTHER PUBLICATIONS

BD Advantage™ 2 PCR Enzyme System User Manual, pp. 1-24, Apr. 11, 2003.*
S.E. Devine et al., Efficient integration of artificial transposons into plasmid targets in vitro: a useful tool for DNA mapping, sequeincing and genetic analysis, Nucleic Acids Research, vol. 22, No. 18, 1994, pp. 3765-3772.

* cited by examiner

*Primary Examiner*—Frank Lu (57) ABSTRACT

The present invention relates to an automated method of transposon-mediated multiplex sequencing of DNA fragments inserted into a vector. It relates more particularity to an increased efficiency in such automated methods, where the increased efficiency is obtained by screening out before the sequencing those constructs in which the transposon inserted into the vector sequence. This prevents a waste of time and resources in performing reactions sequencing the vector instead of the DNA fragments of interest.

16 Claims, 7 Drawing Sheets

GPS-Apra

KpnI (1)
GGTACCCTGTGAATGCGCAAACCAACCCTTGGCAGAACATATCCATCGCGTCCGCCATCTCCAGCAGC
CGCACGCGGCGCATCTCGGGCAGCGTTGGGTCCTGGCCACGGGTGCGCATGATCGTGCTCCTGTCGTT
GAGGACCCGGCTAGGCTGGCGGGGTTGCCTTACTGGTTAGCAGAATGAATCACCGATACGCGAGCGAA
CGTGAAGCGACTGCTGCTGCAAAACGTCTGCGACCTGAGCAACAACATGAATGGTCTTCGGTTTCCGT
GTTTCGTAAAGTCTGGAAACGCGGAAGTCAGCGCCCTGCACCATTATGTTCCGGATCTATGTCGGGTGC
GGAGAAAGAGGTAATGAAATGGCAGATCCCTGGCTTGTTGTCCACAACCGTTAAACCTTAAAAGCTTT
AAAAGCCTTATATATTCTTTTTTTTCTTATAAAACTTAAAACCTTAGAGGCTATTTAAGTTGCTGATTTA
TATTAATTTTATTGTTCAAACATGAGAGCTTAGTACGTGAAACATGAGAGCTTAGTACGTTAGCCATGA
GAGCTTAGTACGTTAGCCATGAGGGTTTAGTTCGTTAAACATGAGAGCTTAGTACGTTAAACATGAGA
                                Sna BI (645)
GCTTAGTACGTGAAACATGAGAGCTTAGTACGTACTATCAACAGGTTGAACTGCTGATCTTCGGATCT
ATGTCGGGTGCGGAGAAGAGGTAATGAAATGGCATCCGGATCTGCATCGCAGGATGCTGCTGGCTAC
CCTGTGGAACACCTACATCTGTATTAACGAAGCGCTGGCATTGACCCTGAGTGATTTTCTCTGGTCCC
GCCGCATCCATACCGCCAGTTGTTTACCCTCACAACGTTCCAGTAACCGGGCATGTTCATCATCAGTAA
CCCGTATCGTGAGCATCCTCTCTCGTTTCATCGGTATCATTACCCCCATGAACAGAAATCCCCCTTACA
CGGAGGCATCAGTGACCAAACAGGAAAAAACCGCCCTTAACATGGCCCGCTTTATCAGAAGCCAGACA
TTAACGCTTCTGGAGAAACTCAACGAGCTGGACGCGGATGAACAGGCAGAGCTCTTACTGTCATGCCA
                                           *NGPS primer*  ←————————————
TCCGTATGTGGGCGGACAATAAAGTCTTAAACTGAACAAAATAGATCTAAACTATGACAATAAAGTC
TTAAACTAGACAGAATAGTTGTAAACTGAAATCAGTCCAGTTATGCTGTGAAAAAGCATACTGGACTT
TTGTTATGGCTAAAGCAAACTCTTCATTTTCTGAAGTGCAAATTGCCCGTCGTATTAAAGAGGGGCGTG
    Not I (1308)
GGGTCGACGCGGCCGCGCCGTATTTGCAGTACCAGCGTACGGCCCACAGAATGATGTCACGCTGAAA
ATGCCGGCCTTTGAATGGGTTCATGTGCAGCTCCATCAGCAAAAGGGGATGATAAGTTTATCACCACC
GACTATTTGCAACAGTGCCGTTGATCGTGCTATGATCGACTGATGTCATCAGCGGTGGAGTGCAATGTC
GTGCAATACGAATGGCGAAAAGCCGAGCTCATCGGTCAGCTTCTCAACCTTGGGGTTACCCCCGGCGG
TGTGCTGCTGGTCCACAGCTCCTTCCGTAGCGTCCGGCCCCTCGAAGATGGGCCACTTGGACTGATCGA
GGCCCTGCGTGCTGCGCTGGGTCCGGGAGGGACGCTCGTCATGCCCTCGTGGTCAGGTCTGGACGACG
AGCCGTTCGATCCTGCCACGTCGCCCGTTACACCGGACCTTGGAGTTGTCTCTGACACATTCTGGCGCC
TGCCAAATGTAAAGCGCAGCGCCCATCCATTTGCCTTTGCGGCAGCGGGGCCACAGGCAGAGCAGATC
ATCTCTGATCCATTGCCCCTGCCACCTCACTCGCCTGCAAGCCCGGTCGCCCGTGTCCATGAACTCGAT
GGGCAGGTACTTCTCCTCGGCGTGGGACACGATGCCAACACGACGCTGCATCTTGCCGAGTTGATGGC
AAAGGTTCCCTATGGGGTGCCGAGACACTGCACCATTCTTCAGGATGGCAAGTTGGTACGCGTCGATT
ATCTCGAGAATGACCACTGCTGTGAGCGCTTTGCCTTGGCGGACAGGTGGCTCAAGGAGAAGAGCCTT
CAGAAGGAAGGTCCAGTCGGTCATGCCTTTGCTCGGTTGATCCGCTCCCGCGACATTGTGGCGACAGC
CCTGGGTCAACTGGGCCGAGATCCGTTGATCTTCCTGCATCCGCCAGAGGGCGGGATGCGAAGAATGC
GATGCCGCTCGCCAGTCGATTGGCTGAGCTCATGAGCGGAGAACGAGATGACGTTGGAGGGGCAAGGT
CGCGCTGATTGCTGGGGCAACACGTGGAGCGGATCGGGGATTGTCTTTCTTCAGCTCGCTGATGATAT
        Spe I (2413)
GCTGACGCTCAATGCCGTTTGGACTAGTGTCGACCAACCAGATAAGTGAAATCTAGTTCCAAACTATT
TTGTCATTTTTAATTTTCGTATTAGCTTACGACGCTACACCCAGTTCCCATCTATTTTGTCACTCTTCCCT
AAATAATCCTTAAAAACTCCATTTCCACCCCTCCCAGTTCCCAACTATTTTGTCCGCCCACACCGTAA
  *SGPS primer* ————————————→
GATGCTTTTCTGTGACT

Figure 2

Figure 3 - GPS-Apra-2uM-URA3-Pj

Kpn I (1)
GGTACCCTGTGAATGCGCAAACCAACCCTTGGCAGAACATATCCATCGCGTCCGCCATCTCCAGCAGCCGCACGCGGCGCATCTCG
GGCAGCGTTGGGTCCTGGCCACGGGTGCGCATGATCGTGCTCCTGTCGTTGAGGACCCGGCTAGGCTGGCGGGGTTGCCTTACTGGT
TAGCAGAATGAATCACCGATACGCGAGCGAACGTGAAGCGACTGCTGCTGCAAAACGTCTGCGACCTGAGCAACAACATGAATGGT
CTTCGGTTTCCGTGTTTCGTAAAGTCTGGAAACGCGGAAGTCAGCGCCCTGCACCATTATGTTCCGGATCTATGTCGGGTGCGGAGA
AAGAGGTAATGAAATGGCAGATCCCTGGCTTGTTGTCCACAACCGTTAAACCTTAAAAGCCTTATATATTCTTTTTTT
CTTATAAAACTTAAAACCTTAGAGGCTATTTAAGTTGCTGATTTATATTAATTTTATTGTTCAAACATGAGAGCTTAGTACGTGAAAC
ATGAGAGCTTAGTACGTTAGCCATGAGAGCTTAGTACGTTAGCCATGAGGGTTTAGTTCGTTAAACATGAGAGCTTAGTACGTTAAA
Sna BI (645)
CATGAGAGCTTAGTACGTGAAACATGAGAGCTTAGTACGTACTATCAACAGGTTGAACTGCTGATCTTCGGATCTATGTCGGGTGCG
GAGAAAGAGGTAATGAAATGGCATCCGGATCTGCATCGCAGGATGCTGCTGGCTACCCTGTGGAACACCTACATCTGTATTAACGA
AGCGCTGGCATTGACCCTGAGTGATTTTTCTCTGGTCCCGCCGCATCCATACCGCCAGTTGTTTACCCCTCACAACGTTCCAGTAACCG
GGCATGTTCATCATCAGTAACCCGTATCGTGAGCATCCTCTCTCGTTTCATCGGTATCATTACCCCCATGAACAGAAATCCCCCTTAC
ACGGAGGCATCAGTGACCAAACAGGAAAAAACCGCCCTTAACATGGCCCGCTTTATCAGAAGCCAGACATTAACGCTTCTGGAGAA
ACTCAACGAGCTGGACGCGGATGAACAGGCAGAGCTCTTACTGTCATGCCATCCGTATGTGGGCGGACAATAAAGTCTTAAACTGA
NGPS primer ←——————————
ACAAAATAGATCTAAACTATGACAATAAAGTCTTAAACTAGACAGAATAGTTGTAAACTGAAATCAGTCCAGTTATGCTGTGAAA
AAGCATACTGGACTTTTGTTATGGCTAAAGCAAACTCTTCATTTTCTGAAGTGCAAATTGCCCGTCGTATTAAAGAGGGGCGTGGGG
Not I (1308)
TCGACGCGGCCGCGAATTCTGAACCAGTCCTAAAACGAGTAAATAGGACCGGCAATTCTTCAAGCAATAAACAGGAATACCAATTA
TTAAAAGATAACTTAGTCAGATCGTACAATAAAAGCTTTGAAGAAAAATGCGCCTTATTCAATCTTTGCTATAAAAAATGGCCCAAAA
TCTCACATTGGAAGACATTTGATGACCTCATTTCTTTCAATGAAGGGCCTAACGGAGTTGACTAATGTTGTGGGAAATTGGAGCGAT
AAGCGTGCTTCTGCCGTGGCCAGGACAACGTATACTCATCAGATAACAGCAATACCTGATCACTACTTCGCACTAGTTTCTCGGTACT
ATGCATATGATCCAATATCAAAGGAAATGATAGCATTGAAGGATGAGACTAATCCAATTGAGGAGTGGCAGCATATAGAACAGCTA
AAGGGTAGTGCTGAAGGAAGCATACGATACCCCGCATGGAATGGGATAATATCACAGGAGGTACTAGACTACCTTTCATCCTACAT
AAATAGACGCATATAAGTACGCATTTAAGCATAAACACGCACTATGCCGTTCTTCTCATGTATATATATATACAGGCAACACGCAGA
TATAGGTGCGACGTGAACAGTGAGCTGTATGTGCGCAGCTCGCGTTGCATTTTCGGAAGCGCTCGTTTTCGGAAACGCTTTGAAGTT
CCTATTCCGAAGTTCCTATTCTCTAGAAAGTATAGGAACTTCAGAGCGCTTTTGAAAACCAAAAGCGCTCTGAAGACGCACTTTCAA
AAAACCAAAAACGCACCGGACTGTAACGAGCTACTAAAATATTGCGAATACCGCTTCCACAAACATTGCTCAAAAGTATCTCTTTGC
TATATATCTCTGTGCTATATCCCTATATAACCTACCCATCCACCTTTCGCTCCTTGAACTTGCATCTAAACTCGACCTCTACATTTTTT
ATGTTTATCTCTAGTATTACTCTTTAGACAAAAAAATTGTAGTAAGAACTATTCATAGAGTGAATCGAAAACAATACGAAAATGTAA
ACATTTCCTATACGTAGTATATAGAGACAAAATAGAAGAAACCGTTCATAATTTTCTGACCAATGAAGAATCATCAACGCTATCACT
TTCTGTTCACAAAGTATGCGCAATCCACATCGGTATAGAATATAATCGGGGATGCCTTTATCTTGAAAAAATGCACCCGCAGCTTCG
CTAGTAATCAGTAAACGCGGGAAGTGGAGTCAGGCTTTTTTTATGGAAGAGAAAATAGACACCAAAGTAGCCTTCTTCTAACCTTAA
CGGACCTACAGTGCAAAAAGTTATCAAGAGACTGCATTATAGAGCGCACAAAGGAGAAAAAAAGTAATCTAAGATGCTTTGTTAGA
AAAATAGCGCTCTCGGGATGCATTTTTGTAGAACAAAAAAGAAGTATAGATTCTTTGTTGGTAAAATAGCGCTCTCGCGTTGCATTT
CTGTTCTGTAAAAATGCAGCTCAGATTCTTTGTTTGAAAAATTAGCGCTCTCGCGTTGCATTTTTGTTTTACAAAAATGAAGCACAGA
TTCTTCGTTGGTAAAATAGCGCTTTCGCGTTGCATTTCTGTTCTGTAAAAATGCAGCTCAGATTCTTTGTTTGAAAAATTAGCGCTCTC
GCGTTGCATTTTTGTTCTACAAAATGAAGCACAGATGCTTCGTTAACAAAGATATGCTATTGAAGTGCAAGATGGAAACGCAGAAAA
TGAACCGGGGATGCGACGTGCAAGATTACCTATTGCAATAGATGCAATAGTTTCTCCAGGAACCGAAATACATACATTGTCTTCCGTA
AAGCGCTAGACTATATATTATTATACAGGTTCAAATATACTATCTGTTTCAGGGAAAACTCCCAGGTTCGGATGTTCAAAATTCAATG
ATGGGTAACAAGTACGATCGTAAATCTGTAAAACAGTTTGTCGGATATTAGGCTGTATCTCCTCAAAGCGTATTCGAATATCATTGA
GAAGCTGCAGCGTCACATCGGATAATAATGATGGCAGCCATTGTAGAAGTGCCTTTTGCATTTCTAGTCTCTTTCTCGGTCTAGCTAG
TTTTACTACATCGCGAAGATAGAATCTTAGATCACACTGCCTTTGCTGAGCTGGATCAATAGAGTAACAAAAGAGTGGTAAGGCCTC
GTTAAAGGACAAGGACCTGAGCGGAAGTGTATCGTACAGTAGACGGAGTATACTAGTATAGTCTATAGTCCGTGGAATTCTCATGTT
TGACAGCTTATCATCGATAAGCTTTTCAATTCAATTCATCATTTTTTTTTATTCTTTTTTTTGATTTCGGTTTCTTTGAAATTTTTTTGA
TTCGGTAATCTCCGAACAGAAGGAAGAACGAAGGAAGGAGCACAGACTTAGATTGGTATATATACGCATATGTAGTGTTGAAGAAA
CATGAAATTGCCCAGTATTCKYRRCCGCWWYTGCACAGAACAAAAACCTGCAGGAAACGAAGATAAATCATGTCGAAAGCTACAT
ATAAGGAACGTGCTGCTACTCATCCTAGTCCTGTTGCTGCCAAGCTATTTAATATCATGCACGAAAAGCAAACAAACTTGTGTGCTTC
ATTGGATGTTCGTACCACCAAGGAATTACTGGAGTTAGTTGAAGCATTAGGTCCCAAAATTTGTTTACTAAAAACACATGTGGATAT
CTTGACTGATTTTTCCATGGAGGGCACAGTTAAGCCGCTAAAGGCATTATCCGCCAAGTACAATTTTTTACTCTTCGAAGACAGAAA
ATTTGCTGACATTGGTAATACAGTCAAATTGCAGTACTCTGCGGGTGTATACAGAATAGCAGAATGGGCAGACATTACGAATGCACA
CGGTGTGGTGGGCCCAGGTATTGTTAGCGGTTTGAAGCAGGCGGCAGAAGAAGTAACAAAGGAACCTAGAGGCCTTTTGATGTTAG
CAGAATTGTCATGCAAGGGCTCCCTATCTACTGGAGAATATACTAAGGGTACTGTTGACATTGCGAAGAGCGACAAAGATTTTGTTA
TCGGCTTTATTGCTCAAAGAGACATGGGTGGAAGAGATGAAGGTTACGATTGGTTGATTATGACACCCGGTGTGGGTTTAGATGACA
AGGGAGACGCATTGGGTCAACAGTATAGAACCGTGGATGATGTGGTCTCTACAGGATCTGACATTATTATTGTTGGAAGAGGACTAT
TTGCAAAGGGAAGGGATGCTAAGGTAGAGGGTGAACGTTACAGAAAAGCAGGCTGGGAAGCATATTTGAGAAGATGCGGCCAGCA
AAACTAAAAAACTGTATTATAAGTAAATGCATGTATACTAAACTCACAAATTAGAGCTTCAATTTAATTTATATCAGTTATTACCC
GGGAATCTCGGTCGTAATGATTTTTATAATGACGAAAAAAAAAAAATTGGAAAGAAAAAGCTTTAATGCGGTAGTTTATCACAGT
Not I (4808)
TAAATTGCTAACGCAGTCAGGCACCGGCCGCCGCCGTATTTGCAGTACCAGCGTACGGCCCACAGAATGATGTCACGCTGAAAA
TGCCGGCCTTTGAATGGGTTCATGTGCAGCTCCATCAGCAAAAGGGGATGATAAGTTTATCACCACCGACTATTTGCAACAGTGCCG
TTGATCGTGCTATGATCGACTGATGTCATCAGCGGTGGACGTGCAATGTCGTGCAATACGAATGGCGAAAAGCCGAGCTCATCGGTCA
GCTTCTCAACCTTGGGGTTACCCCCGGCGGTGTGCTGCTGGTCCACAGCTCCTTCCGTAGCGTCCGGCCCCTCGAAGATGGGCCACTT
GGACTGATCGAGGCCCTGCGTGCTGCGCTGGGTCCGGGAGGGACGCTCGTCATGCCCTCGTGGTCAGGTCTGGACGACGAGCCGTTC
GATCCTGCCACGTCGCCCGTTACACCGGACCTTGGAGTTGTCTCTGACACATTCTGGCGCCTGCCAAATGTAAAGCGCAGCGCCCAT
CCATTTGCCTTTGCGGCAGCGGGGCCACAGGCAGACGAGATCATCTCTGATCCATTGCCCCTGCCACCTCACTCGCCTGCAAGCCCG
GTCGCCCGTGTCCATGAACTCGATGGGCAGGTACTTCTCCTCGGCGTGGGACACGATGCCAACACGACGCTGCATCTTGCCGAGTTG
ATGGCAAAGGTTCCCTATGGGGTGCCGAGACACTGCACCATTCTTCAGGATGGCAAGTTGGTACGCGTCGATTATCTCGAGAATGAC
CACTGCTGTGAGCGCTTTGCCTTGGCGGACAGGTGGCTCAAGGAGAAGAGCCTTCAGAAGGAAGGTCCAGTCGGTCATGCCTTTGCT
CGGTTGATCCGCTCCGCGACATTGTGGCGACAGCCCTGGGTCAACTGGGCCGAGATCCGTTGATCTTCCTGCATCCGCCAGAGGGC
GGGATGCGAAGAATGCGATGCCGCTCGCCAGTCGATTGGCTGAGCTCATGAGCGGAGAACGAGATGACGTTGGAGGGGCAAGGTCG
CGCTGATTGCTGGGGCAACACGTGGAGCGGATCGGGGATTGTCTTTCTTCAGCTCGCTGATGATATGCTGACGCTCAATGCCGTTTG
Spe I (5913)
GACTAGTGTCGACCAACCAGATAAGTGAAATCTAGTTCCAAACTATTTTGTCATTTTTAATTTTCGTATTAGCTTACGACGCTACACC
CAGTTCCCATCTATTTTGTCACTCTTCCCTAAATAATCCTTAAAAACTCCATTTCCACCCCTCCCAGTTCCCAACTATTTTGTCCGCC
CACACCGTAAGATGCTTTTCTGTGACT     SGPS primer ——————————→

Figure 4. Results of a quick screen of various PCR kits tested during the 384-well optimization process.

Figure 5. PCR results showing the appearance of a 9 kbp band believed to be the amplified product of vector containing the transposon. This upper band is the result of an excessive extension time.

Figure 6. Results of 48 °C and 68 °C gradient PCR tested with 30, 35, 40, and 45 cycles.

Figure 7: Correlation between electrophoresis results and PICOGREEN® staining for determining significant amounts of dsDNA

TRANSPOSON MEDIATED MULTIPLEX SEQUENCING

PRIORITY CLAIM

This application is a 35 U.S.C. § 371 filing of PCT Application number PCT/US01/21269 filed on Jul. 5, 2001, which claims the benefit of U.S. Provisional Application number 60/216,381 filed on Jul. 7, 2000.

FIELD OF THE INVENTION

The present invention relates to an automated method of transposon-mediated multiplex sequencing of DNA fragments inserted into a vector. It relates more particularly to an increased efficiency in such automated methods, where the increased efficiency is obtained by screening out before the sequencing those constructs in which the transposon inserted into the vector sequence. This prevents a waste of time and resources in performing reactions sequencing the vector instead of the DNA fragments of interest.

BACKGROUND OF THE INVENTION

The enormous wealth of information that has been acquired from genomic and expressed sequence tag (EST) sequencing in the last 10 years has contributed significantly to efforts to clone full-length cDNA representatives. Although it is anticipated that genomic sequencing projects from human and mouse will be completed in the near future, the transcriptome of these species will remain ambiguous for some time. The complexities involved in predicting, with complete certainty, the splicing program of mRNAs from genomic sequences have compelled additional genomic research focused on obtaining the sequences of full-length cDNAs. In addition, full-length cDNA sequencing efforts are also required for the confirmation of cDNA sequences after methods that involve amplification of the cDNA have been employed for cloning. This scenario is particularly prevalent in genomic centers that are focused on validating gene targets for drug discovery efforts. Clearly, after great expense and effort has been expended, it would be senseless for a putative target to fail the validation process simply because the coding sequence of the target gene was incorrect. Therefore, approaches are required at genomic centers to sequence large numbers of full-length clones quickly, inexpensively, and accurately. For this purpose, Applicants have created a new, integrated high-throughput process called transposon expedited multiplex sequencing (TEMS).

In the last 20 years, many methods have been developed for sequencing large inserts to plasmids. However, many of these methods were cumbersome and could not be transferred to high-throughput, automated systems. Sequencing by primer walking is slow, expensive, and often fails since primers are designed to the sequence in a poorly characterized region. Similarly, sequencing by creating a collection of clones by exonuclease digestion from the ends of the target clone is slow, clone specific, and extremely sensitive to the purity and integrity of the template DNA. In addition, the success rate using this approach is quite variable. Shotgun sequencing of clones is a higher-throughput method, however it requires isolating the insert from each clone and then recloning smaller fragments generated by a wide variety of methods. Additionally, shotgun libraries that utilize restriction digests result in a cloning bias and subsequently a non-random distribution of DNA sequence data.

Transposon-mediated sequencing can be done by pooling a large number of vectors containing target DNA sequences and randomly inserting a transposon with sequencing primers on each end into the constructs. See Devine, S. E., Boeke, J. E. (1994) *Efficient integration of artificial transposons into plasmid targets in vitro: a useful tool for DNA mapping, sequencing and genetic analysis*, Nucleic Acids Research, pp. 3765-3772; or Kimmel, B., M. J. Palazzola, C. Martin, J. D. Boeke, and S. E. Devine, 1997, *Transposon-mediated DNA sequencing. In Genomic Analysis: A laboratory manual* (ed. E Green, B. Birren, R. Myers, and P. Hieter), Cold Spring Harbor Laboratory Press, Cold Spring Harbor, N.Y., for a description of the method. Traditionally, this method was cumbersome since it required moving plasmids through different host strains for the cloning and transposon-insertion steps. Recently however, several commercial molecular biology vendors have developed in vitro transposition systems to take advantage of the random insertion of a modified transposon (ie. Tn5 etc.). Unfortunately, some of these systems result in a high background of false positives, and are difficult to use with methods to screen positive clones by polymerase chain reaction ("PCR"). Applicants have utilized several of these transposon based sequencing methods and have not experienced any of these difficulties with a modified version of the in vitro GPS-1 transposition system from New England Biolabs. Nevertheless, transposon insertions cannot be directed exclusively to the target DNA of interest and appear in the vector with a high frequency. In an effort to solve this problem and increase the efficiency of transposon facilitated sequencing, Applicants have developed a unique, high-throughput procedure called transposon expedited multiplex sequencing (TEMS).

Accordingly, it is an object of this invention to provide a high-throughput, efficient, and inexpensive process for the sequencing of DNA fragments.

It is a further object of this invention to provide a high-throughput, efficient and inexpensive process for transposon-mediated sequencing of target DNA fragments which minimizes the amount of non-target DNA sequence generated.

It is yet another object of this invention to provide a PCR-based screen to distinguish between the desired constructs with transposons inserted into the target DNA sequence and the undesired constructs with transposons inserted elsewhere.

SUMMARY OF THE INVENTION

The present invention meets the above objects by providing the following method, which may be automated for further convenience. Multiple DNA target sequences, each cloned into a vector, are pooled and selectable transposons with sequencing primers on each end are inserted randomly into the DNA target-containing vectors. Selected, transposon- and DNA target sequence-containing vectors are then individually screened using a PCR reaction to identify those vectors which have transposons located in the DNA target sequence. The PCR reaction uses primers located at each end of the vector sequence and is optimized to provide sufficient extension time for the PCR polymerase to efficiently produce a product the length of the vector, but insufficient extension time for the PCR polymerase to efficiently produce a product the length of the vector plus the transposon. Therefore, significant amounts of PCR product will only be produced for vectors containing the transposon in the DNA target sequence and not the vector. The presence or absence of a significant amount of PCR product for each PCR reaction can be quickly determined by the use of a quantitative fluorescent dye selective for double stranded DNA ("dsDNA"). Vectors identified by a significant PCR product in the prescreen are then individually sequenced using the sequencing primers on each end of the transposon to read out into each DNA target sequence. The raw DNA target sequences of individual sequencing reactions can be combined to determine the full sequence of each of the DNA targets in the pool.

The parallel processing of clones greatly increases the speed in which reactions can be set up and sequenced. Additionally, the process does not rely on any particular vector and does not require any recloning steps. Most important for overall efficiency, sequencing of the vector backbone is minimized or eliminated with the screening step. Automation of each of the steps of the instant process can be readily achieved using equipment available to those in the art of automated DNA sequencing.

BRIEF DESCRIPTION OF THE DRAWINGS

FIG. 2 shows the sequence of GPS-Apra transposon vector (SEQ ID NO: 1).

FIG. 3 shows the sequence of GPS-Apra-2 μm-URA3 transposon vector SEQ ID NO: 2).

DEFINITIONS

As Used Herein:

A "vector" is any DNA construct which replicates in a cell and has an insertion site at which unknown DNA sequences can be inserted.

"Selectable", in reference to a vector or transposon, means that the vector or transposon carries a phenotype that can be used to identify cells transformed with the vector or transposon. Preferably, the phenotype allows the transformed cells to survive in conditions in which non-transformed cells cannot.

A "target DNA" or "target DNA sequence" is a DNA molecule of known or unknown sequence which the operator of the method desires to sequence.

A "representative number of individual transformants" is a minimum number of individual transformants which ensures that for each target DNA in the pool there will be a sufficient number of transformants containing insertions of the transposon into that target DNA to provide a desired number of independent sequencing determinations of each base in that target DNA.

"Substantial amounts of dsDNA" in regard to PCR products is an amount of dsDNA that exceeds a predetermined threshold. The predetermined threshold can be identified by evaluating the variability of PCR products found within PCR reactions with several constructs which are known to contain the transposon inside or outside the vector sequence.

DETAILED DESCRIPTION OF THE PREFERRED EMBODIMENTS

The present invention provides a method that can be efficiently automated for sequencing multiple target DNAs in parallel. In the method, each target DNA sequence is inserted into a selectable vector, preferably a plasmid, at identical insertion points in the vector sequence. It is important that all target DNAs are inserted into the same vector or, if different vectors are used, that each vector is substantially the same size and has identical sequences around the insertion point so that one set of primers can be used to amplify all the vectors by PCR reaction.

The vectors containing each of the multiple target DNA sequences are pooled in ratios based on the length of each target DNA sequence, so the pool contains substantially equal amounts of each kb of each target DNA sequence. The ratios for each vector to be included in the pool can be determined by determining the lengths of each target DNA sequence (for instance, by electrophoresis against standards size markers on an agarose gel), and adding to the pool a set amount of each vector for every kb in length of the target DNA sequence in that vector.

A transposon-insertion reaction is then performed on the pool to randomly insert a selectable transposon into the target-DNA containing vectors. Although this step could be performed by traditional, in vivo, transposon insertion, that would require moving a plasmid through more than one cell type. In vitro transposon-insertion reactions are much simpler and faster. The transposon must carry a selectable marker and must be of sufficient size to enable PCR conditions to be established that efficiently multiply a dsDNA fragment the size of the vector, but do not significantly multiply a dsDNA fragment the size of the vector plus the transposon. Preferably, the transposon is about equal to or greater than the vector in length. Most preferably, the transposon is equal to or greater than ¾ the length of the vector. Particularly preferably, the transposon is equal to or greater than ⅔ the length of the vector. Where the vector is a bacterial plasmid, the transposon is preferably at least about 3 kb, most preferably at least about 4 kb and particularly preferably greater than or equal to about 5 kb.

The pool of vectors from the transposon-insertion reaction is then used to transform cells and the transformants are grown under conditions which select for the transposon. Selected transformants are isolated and grown into cultures. The number of isolated transformants grown into cultures depends on the number and size of target DNA sequences in the pool. Enough transformants must be isolated and grown to ensure that for each target DNA sequence, the isolated transformants will include enough individual insertions of the transposon into that particular target DNA sequence to provide several fold independent sequence determinations of each and every base in that target DNA sequence. To ensure against errors, those of skill in the art often seek to obtain a 6-fold coverage of sequence data, although they may opt for more or less, as the situation merits. When attempting to obtain 6-fold coverage, as a general rule of thumb, 18 clones will need to be actually sequenced per 1 kb of nucleotides to obtain this coverage. However to actually sequence 18 clones, a greater number of transformants will have to isolated and grown, because the transposon will not have integrated into the target DNA in every case, but will have randomly inserted over the whole target DNA-containing vector. Therefore, the number 18 is multiplied by the likelihood that the transposon inserted into the target DNA sequence. So, to obtain 6-fold sequencing coverage, for each target DNA sequence in the pool, a number of transformants to be isolated is equal to: the length of the target DNA sequence in kb times 18, times the ratio (size of vector)/(size of DNA target sequence).

Each culture from a selected transformant then has a PCR reaction performed on its DNA. The PCR reaction uses primers complementary to the 3' ends of the vector sequence at the insertion point, which allow PCR multiplication of a fragment the size of the entire vector sequence. The reaction conditions of the PCR reaction are optimized to efficiently produce a fragment the length of the vector, but not to efficiently produce a fragment the length of the vector plus the transposon. The optimization of PCR conditions for any particular vector and transposon combination according to this invention can be determined by one of skill in the art through routine experimentation, as guided by such reference works as Kimmel, B., M. J. Palazzola, C. Martin, J. D. Boeke, and S. E. Devine, 1997, *Optimizing PCR Assays, Methods for Improving PCR, Detecting and Characterizing PCR products, Protocols for Detecting and Characterizing PCR Products. In Genomic Analysis: A laboratory manual* (ed. E Green, B. Birren, R. Myers, and P. Hieter), Cold Spring Harbor Laboratory Press, Cold Spring Harbor, N.Y.; and Cha, R. S. and Thilly, W. G. (1995) in: *PCR Primer*, Dieffenbach, C. W. and Dveksler, G. S. (eds.), CSH Press, New York. The particular DNA polymerase used for PCR should not be limiting for the method, although the choice of polymerase may help to optimize the reaction. Generally, the elongation temperature and/or time of the PCR are varied to achieve the desired exclusion of the vector plus transposon sized product. For a demonstration of optimization, see Example 2.

The amount of product produced in each PCR reaction is then measured, preferably optically. Optical measurement could be made by any method which distinguishes dsDNA from nucleotides, but is preferably made using a fluorescent dye specific for dsDNA. dsDNA specific dyes include the bis-benzimide dye Hoechst 33528 and the cyanine dyes of Molecular Probes, Inc, Eugene, Oreg., including PICOGREEN®. PICOGREEN® is preferred, due to its sensitivity and selectivity for dsDNA. The measured value of fluorescence is compared to a predetermined threshold level for determining whether a significant amount of dsDNA PCR product is present. The threshold level of fluorescence is set experimentally using positive and negative control PCR templates of the size of the vector alone and the vector plus the transposon, under the same PCR conditions that will be used to screen the isolated transformants.

Those transformants corresponding to PCR reactions which did not produce substantial amounts of dsDNA are not sequenced, because they contain the transposon in the vector sequence. Transformants corresponding to PCR reactions which produce substantial amounts of dsDNA contain the transposon in the target DNA sequence and are sequenced. Two sequencing reactions are performed for each transformant, using primers from each end of the transposon to read the sequence of the target DNA sequence surrounding the transposon. The sequencing reactions can be performed by any of the known methods of the art.

Once sequence data has been collected from all the transformants which passed the PCR screen, the sequences must be assembled into all the individual members of the pool of target DNA sequences. This can be accomplished by methods of computer sequence analysis known in the art, and the exact manner is not limiting on this invention.

The advantages of the instant method include speed, efficiency and an ability to automate the process. Particularly, the instant method provides a quick PCR screen that allows for elimination of those unproductive transformants which have the transposon inserted into the vector sequence and would yield mainly vector sequences if sequenced. The PCR screen is fast, can be automated and does not require any isolation of the PCR product, such as running an agarose gel to determine its size. The use of a pool of target DNAs allows a single transposon reaction and a single transformation to be performed, instead of requiring one for each target DNA sequence.

EXAMPLES

Example 1

Choosing a Transposon to Fit a High-Throughput Screening Process

Original Transposon from New England Biolabs

The Genome Priming System Kit from New England Biolabs, 32 Tozer Road, Beverly, Mass. 01915 ("NEB") was used to initially prove that a transposon inserted randomly into DNA targets could be an efficient way to completely sequence the targets with a great degree of accuracy. Supplied with the kit was one of two transposons that contained the kanamycin resistance gene. However, kanamycin is a fairly common resistance marker, and if a target DNA sequence was already cloned into a kanamycin-selectable vector, then either a different transposon or recloning of the target DNA sequence would be required. The kit provided another transposon that contained the chloramphenicol resistance marker, but that, too, is fairly common. Therefore, the transposon should be modified to contain an uncommon resistance marker, such as apramycin, to avoid additional cloning steps and reduce human error in choosing the correct transposon for each DNA target. The GPS-Apra transposon (FIG. 2) was constructed by modifying the NEB pGPS1 transposon.

Screening Method Using the Modified Transposon, GPS-Apra

Initial experiments showed that a screening process could identify from transformants selected for the transposon those transformants containing the transposon in the target DNA sequence and not the vector. This reduces costs by eliminating unproductive sequencing of the vector sequence. The original NEB pGPS1 transposon was 2.614 kb with ~1.7 kb of that, with priming sites at each end, being randomly inserted into the target DNA. By PCR amplification of the 3.0 kb vector using complement M13F and complement M13R primers, two distinct PCR products could be visualized on a slab gel. A 3.0 kb PCR product indicates that the transposon must be in the target DNA sequence, since the vector is 3.0 kb. A 4.7 kb PCR product indicates a vector (3.0 kb) containing the transposon (1.7 kb). Therefore, clones containing the transposon in the target DNA sequence could be identified by the presence of 3.0 kb PCR products on the gel.

To demonstrate identification of clones containing the transposon in the insert, colonies were selected from the transformation following the transposon reaction and inoculated into media containing both antibiotics for selection, apramycin and the plasmid antibiotic. The culture was grown up overnight and PCR was done the following day by kerplunking approximately 1 ul of culture into a PCR cocktail in a 96 well plate. The PCR cocktail included the Amplitaq enzyme and reagents from PE Corporation, PE Corporation, 761 Main Avenue, Norwalk, Conn. 06859. The conditions for PCR were standard {95 C for 5 min, (95 C for 30 sec, 54 C for 1 min, 72 C for 6 min, 30 cycles), 72 C 1 min, 4 C forever}. After completion of the cycle (approximately 2.5 hr), gel electrophoresis was done using 8 ul of the 50 ul PCR reaction on a standard size gel. There was a clearly detectable size distinction between the PCR products from vector sequence without the transposon and vector sequence including the transposon.

To maintain a high-throughput for the sequencing reactions, however, electrophoresis would have to occur on large gels that could hold hundreds of samples at one time. On these large gels, the difference between a 3 kb and a 4.7 kb fragment would be difficult to reproducibly detect with an automated system. Also, gel electrophoresis was very time consuming and would interfere with performing the screen in a high-throughput manner.

In a search for other, high-throughput methods, fluorescent detection of dsDNA was settled on as reproducible and less time consuming. The PICOGREEN® assay seemed particularly convenient. However, fluorescent detection of dsDNA cannot distinguish between different size fragments, so the PCR reaction had to be altered so that the presence or absence of any PCR product indicates the position of the transposon in the target DNA containing vector. If only clones with the transposon in the target DNA sequence produced a dsDNA PCR product, then the PICOGREEN® dsDNA dye would fluoresce at a high level for only the desired clones. The wells that contain the transposon in the vector would not amplify a significant dsDNA product and would result in a low level of fluorescence. A cutoff level of fluorescence between desired and undesired clones can be determined by the use of known samples.

A variety of PCR conditions were tested by lowering the elongation temperature, but the 4.7 kb band would not consistently drop out, without having an increase of false positives. It was decided that if the transposon could be modified again to greatly increase its size, then PCR conditions could be developed that would consistently drop out the upper, transposon-containing band, thereby lowering the false positive rate. A large "stuffer" gene that would not effect the transposon reaction in a negative way was sought. A yeast 2 um plasmid with the URA3 gene met the size criteria and could also be used in yeast experiments in the future. Therefore, a GPS-Apra-2 um-URA3 transposon plasmid (FIG. 3) was constructed having a total size of 6.1 kb, including the transposon of ~5.0 kb. The PCR conditions were altered successfully to drop out the clones with the transposon in the vector and the transposition reaction was not affected. See Example 2.

Example 2

Optimization of PCR Conditions to Reduce False Negative and False Positive Results Basic PCR Concept This screen is based on PCR cycling conditions that have been specifically optimized to amplify a 3.9 kbp fragment of the entire vector DNA. In this case, the vector was PCR4Blunt-TOPO from Invitrogen, 1600 Faraday Ave, Carlsbad, Calif. 92008. If the vector has the 5 kbp transposon inserted into it, its size will be increased to 8.9 kbp, which is too large to be amplified under the optimized PCR conditions.

Figure 1:
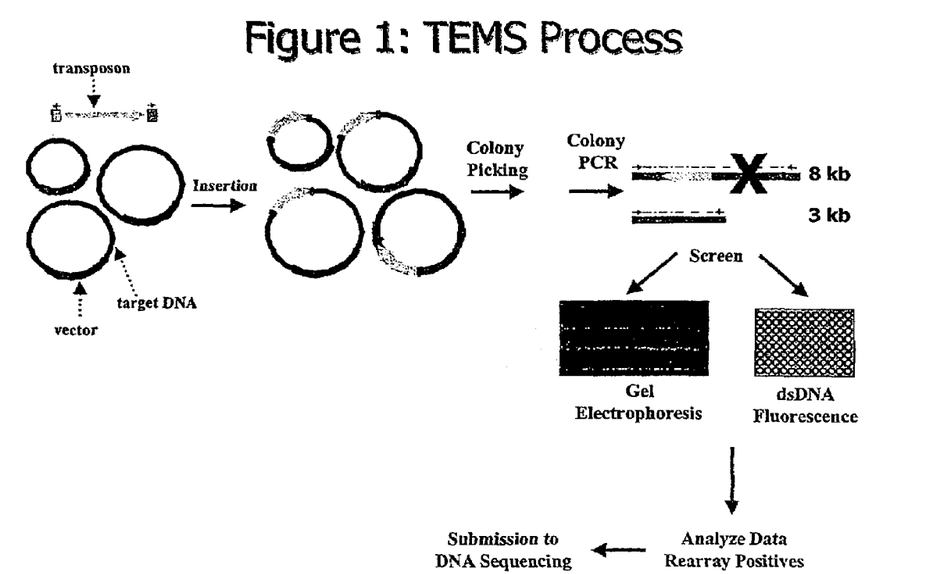
FIG. 1 is a diagram of the steps of TEMS.

The primer sequences selected to amplify the vector portion of the Jones are the complement sequences of the universal primers M13F(−20) and M13R. The sequences are as follows 5'-ACTGGCCGTCGTTTTAC-3' SEQ ID NO: 3) and 5'-CATGGTCATAGCTGTT-3' (SEQ ID NO: 4). This amplification is illustrated in FIG. 1.

Background on the Development of the 384-Well Format

In order to screen transposon reactions from pools containing multiple clones it was necessary to develop a screen that was both quick and cost efficient. Initial development attempts were based on the 96-well protocol. To change to a 384-well plate, all reagent volumes were halved to accommodate the smaller well volume. However, these conditions proved to be less than ideal due to the high number of PCR failures that were being observed. A search for PCR reagents and conditions that were more robust for this format was undertaken. The results of experiments that tested a wide range of enzymes and thermocycling conditions will be described in the following sections.

384-Well PCR Optimization Process

Polymerase Selection

Figure 4:
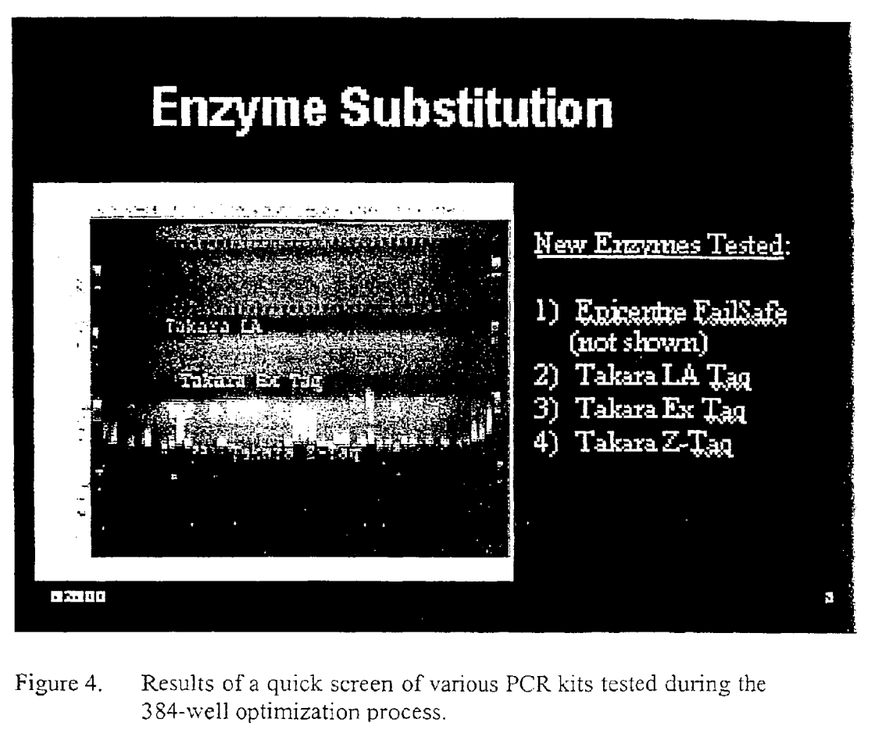
FIG. 4 is a picture of an electrophoresis gel stained to show the products of PCR reactions using various polymerases to multiply the vector portions of the transposon- and target- DNA-containing vectors.

A quick screening of a variety of PCR kits from several vendors was done to determine a 384-well replacement for the PE Corporation AmpliTaq polymerase that had been used in the 96-well format. The following pcr kits were tested: Clontech's Advantage cDNA PCR kit, Epicentre's Failsafe PCR system, and three kits from Takara; LA Taq, Ex Taq, and Z Taq. (Clontech Laboratories Inc. is located at 1020 East Meadow Circle Palo Alto, Calif. 94303-4230; Epicentre Technologies is located at 1402 Emil Street, Madison, Wis. 53713 ; and Takara Shuzo Co., LTD has a business address of Biomedical Group Seta 3-4-1, Otsu, Shiga, 520-2193, Japan.) Samples tested represented 30 pooled DNA targets. They were cloned into pBluescript SK—(3.0 kb) from Stratagene, 11011 North Torrey Pines Road, La Jolla, Calif. 92037. The growth time was 20 hr in 384 well format. Based on preliminary data the Z-taq system was chosen as the enzyme to pursue due to properties it possessed which made it ideal for use in a high-throughput system like TEMS. See FIG. 4, which shows a stained electrophoresis gel on which the PCR products of the samples have been run.

Reagent Optimization

It was also desirable to decrease the cost per reaction of the PCR screen. Table 2, shown below, summarizes the various experiments that were done to test the amount by which each of the various reagents could be lowered without compromising the results.

TABLE 2

Table summarizing the various PCR cocktail ingredients that were tested during the optimization process.

| Variable Tested | Condition Tested | Optimal Result |
|---|---|---|
| Z- Z-Taq polymerase | 0.625, 0.313, 0.156 Units | 0.313 Units |
| 10X Z-Taq Buffer | 1x, 0.5x | 1x |
| Primers | 2.5, 5, 10 pmol | 5 pmol |
| Primers | cM13f & cM13r cT3 & cT7 | cM13f & cM13r |
| dNTP's | 100, 150, 200 µM | 150 µM |

Based on the above experiments the following optimized reaction cocktail mix (per sample) was determined:

ddH$_2$0: 17.875 µL

10× Z-Taq buffer: 2.5 µL dNTP mixture: 1.5 µL template DNA: 1 µL (deposited using a Kerplunker #96/384, manufactured by Nalge Nunc International, 75 Panorama Creek Drive, Rochester, N.Y. 14625, and Pin Replicator #250520/250393)

Z-Taq DNA polymerase: 0.125 µL (0.3125 Units)
cM13f (5 pmol/µL): 1 µL
cM13r (5 pmol/µL): 1 µL Optimization of Thermocycler Conditions Initial thermocycling conditions used were based on recommendations found in the Takara literature. These conditions were:

| | | |
|---|---|---|
| 1. denature: | 98° C. for 5 seconds | |
| 2. anneal: | 55° C. for 10 seconds | |
| 3. extension: | 72° C. for 60 seconds (15.4 seconds/kb) | |
| 4. go to 1, 30 times | | |
| 5. 4° C. until the PCR reaction is evaluated. | | |

Figure 5:
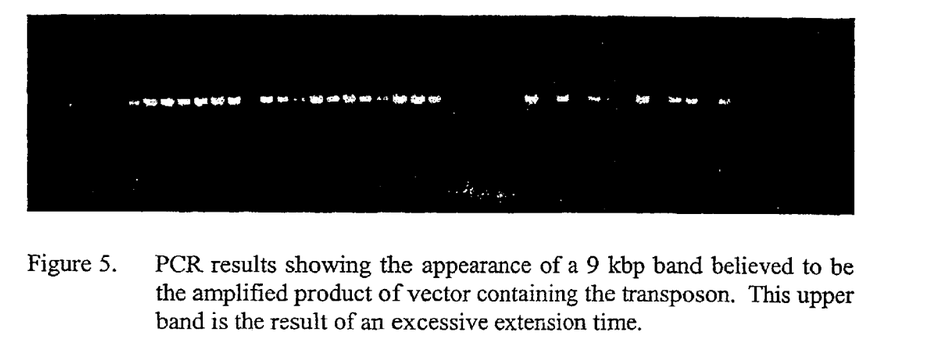
FIG. 5 is a picture of an electrophoresis gel stained to show the products of PCR reactions having too great an extension time to eliminate an approximately 9 kb product.

The results of using these conditions are shown in FIG. 2. From that data, it was decided that the annealing temperature should be lowered so as to try and decrease the reaction specificity and thus increase the number of positives that are amplified. In the next experiment the annealing temperature was lowered to 52° C. Although this helped with the overall reaction results, it was discovered that using an extension time of 15.4 seconds per kbp resulted in the amplification of vector containing the transposon insertion. See FIG. 5, which shows a stained electrophoresis gel on which PCR products from 47 transformants selected after transposon insertion in target DNA-containing pBluescript SK- and grown for 20 hours in wells of a 384 well plate were run. The appearance of a 9 kbp band, believed to be the amplified product of vector containing the transposon, is the result of an excessive extension time.

Figure 6:
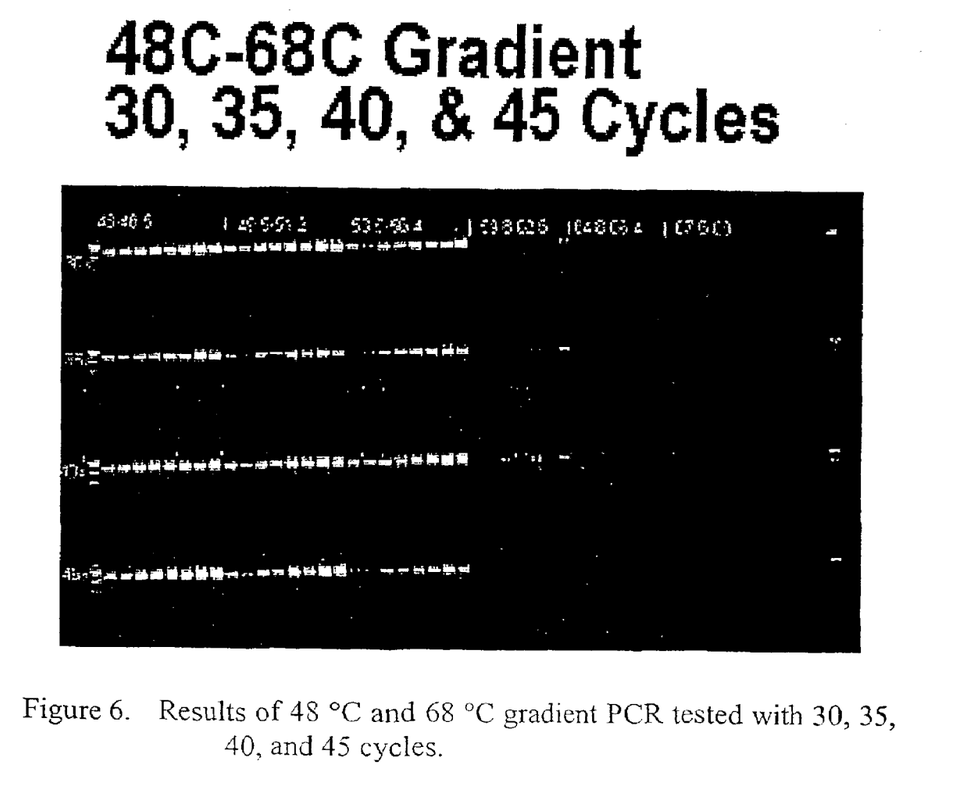
FIG. 6 is a picture of an electrophoresis gel stained to show the products of PCR reactions at a variety of extension temperatures and having different numbers of cycles.

Additionally, an annealing temperature gradient between 48° C. and 68° C. was tested to confirm that 52° C. was indeed the optimal temperature to use for this PCR. In the same experiment the number of cycles was also tested. 30, 35, 40, and 45 cycles were tested. From the results of that experiment it was determined that the number of cycles need to remain low to avoid background noise. From the 48° C. and 68° C. gradient the 52° C. annealing temperature was reconfirmed as being optimal. The temperature is not too low that it becomes non-specific and not too high that it risks approaching the 56° C. temperature at which the PCR begins to fail. These results are shown in FIG. 6, a picture of a stained electrophoresis gel, where each depicted product represents amplification of the control pBluescript SK- vector at 2.5 ng per well, in a 384 well format with 25 ul PCR cocktail volume. Based on the above data, the thermocycling conditions were determined to perform optimally using the following cycle.

| | |
|---|---|
| 1. denature: | 98° C. for 5 seconds |
| 2. anneal: | 52° C. for 10 seconds |
| 3. extension: | 72° C. for 30 seconds (7.7 seconds/kb) |
| 4. go to 1, 35 times | |
| 5. 4° C. until evaluation of the PCR reaction. | |

Since evaporation was found to be a problem in the 384-well plates, rubber 'P' seals from MJ Research, 590 Lincoln Street, Waltham, Mass. 02451, are placed over sealed plates before thermocycling begins. Along with this, and as recommended by the manufacturer, the lid temperature is set to 85° C.

Table 3, shown below, provides a summary of the various PCR thermocycling conditions tested during the optimization process.

TABLE 3

Summary of the PCR thermocycling conditions that were tested during the optimization.

| Variable Tested | Condition Tested | Optimal Result |
|---|---|---|
| Annealing Temperature | 38° C.–68° C. | 52° C. |
| PCR cycle | 30, 35, 40, 45 | 35 |

Screening for Positive Clones Using the dsDNA Quantitation Reagent PICOGREEN®

To bypass the labor-intensive task of gel electrophoresis, the TEMS PCR screen utilizes the dsDNA quantitation reagent, PICOGREEN®. The PICOGREEN® is diluted to a working dilution of 1:150 in 1× TE buffer. This dilution was found to be optimal, although it is slightly more concentrated than the 1:200 dilution recommended in the manufacturer's protocol.

25 µL per well of 1:150 PICOGREEN® is aliquoted into black 384-well plates using a Robbins Hydra 96 Dispenser from Robbins Scientific, 1250 Elko Drive, Sunnyvale, Calif. 94089-2213. 5 µL per well of each PCR reaction is then added to the PICOGREEN®, again using the Hydra Dispenser. The plate is then immediately placed into a Molecular Dynamics Gemini Fluorescence Plate Reader and the plate is then mixed for 10 seconds before its fluorescence signal is measured.

For the assay to function as a screen, there must be a clear difference in the fluorescence signal between positive and negative wells. PCR product amounts of 1.3, 2.5, 5, and 10 µL were tested to determine the greatest assay range of positive signal to background. Results showing that 5 µL of PCR product into 25 µL of PICOGREEN® is the optimal condition to use is shown in Table 4.

TABLE 4

Fluorescence signal detected using the PICOGREEN ® assay with various amounts of PCR product. The 24 PCR products are from samples representing a pool of 11 DNA targets with a sizes up to 4.5 kb cloned into the vector PCR4Blunt-TOPO. The transposon used was pGPS-Apra-2 uM-URA3.

| uL PCR | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1.3 | 353 | 287 | 206 | 987 | 180 | 345 | 1734 | 351 | 171 | 312 | 309 | 237 | 1102 | 308 |
| 2.5 | 839 | 827 | 495 | 1924 | 412 | 751 | 2941 | 694 | 397 | 710 | 711 | 413 | 2129 | 541 |
| 5 | 1489 | 1503 | 835 | 2769 | 635 | 1450 | 3703 | 1640 | 813 | 1220 | 1447 | 882 | 2991 | 1198 |
| 10 | 1806 | 2234 | 1775 | 3023 | 1354 | 2099 | 3870 | 2112 | 1378 | 2095 | 1909 | 1746 | 3401 | 1882 |

TABLE 4-continued

Fluorescence signal detected using the PICOGREEN ® assay with various amounts of PCR product. The 24 PCR products are from samples representing a pool of 11 DNA targets with a sizes up to 4.5 kb cloned into the vector PCR4Blunt-TOPO. The transposon used was pGPS-Apra-2 uM-URA3.

| uL PCR | 15 | 16 | 17 | 18 | 19 | 20 | 21 | 22 | 23 | 24 | high-low |
|---|---|---|---|---|---|---|---|---|---|---|---|
| 1.3 | 202 | 245 | 843 | 134 | 126 | 318 | 223 | 308 | 635 | 223 | 1608 |
| 2.5 | 456 | 549 | 1713 | 313 | 217 | 634 | 407 | 690 | 1434 | 552 | 2724 |
| 5 | 934 | 1003 | 2560 | 624 | 552 | 1259 | 1112 | 873 | 2341 | 1116 | 3151 |
| 10 | 1681 | 1574 | 2902 | 1197 | 983 | 1637 | 1642 | 1560 | 2967 | 1333 | 2887 |

The signal output generated by the fluorescence reader is then exported to a histogram display, and a cutoff value for positive clones is assigned from the histogram. Using the current conditions, the cutoff generally falls between 1000-1500.

A Genesis RSP 150 TECAN robotics station (TECAN U.S. INC., P.O. Box 13953, Research Triangle Park, N.C. 27709) was used to generate 96-deep-well plates containing cells from the clones identified by the screen as having the transposon in the target DNA sequence. Cells from each positive clone are placed in Superbroth and the appropriate antibiotics (dual selection) in one of the wells. These plates are grown and then the cultures are submitted for automated sequencing.

Example of the Optimized PCR Screen Technique for 384-Well Plates

Use Q-Bot to pick colonies of the transposon containing clones into Genetix 384-well shallow-well plates containing 65 μL per well of Superbroth plus appropriate antibiotic. Place plates into a humidified 37° C. incubator for 19-22 hours. Aliquot 25 μL per well of sterile 50% glycerol into the growth plates using a Multidrop 384 115V liquid dispenser (Labsystems Inc., 8 East Forge Parkway, Franklin Mass. 02038). Using the glycerol plate as the template, set-up PCR using the following recipe:

ddH$_2$0: 17.875 μL
10× Z-Taq buffer: 2.5 μL
dNTP mixture: 1.5 μL
template DNA*: 1 μL (using the Kerplunker, pin-tool)
Z-Taq DNA polymerase: 0.125 μL (0.3125 Units)
cM13f (5 pmol/μL): 1 μL
cM13r (5 pmol/μL): 1 μL
*To ensure that the Kerplunker is sterile it should be stored in 70% ethanol and flamed before use.

Placed the PCR reaction plate into a thermocycler and start the following cycle:

1. denature: 98° C. for 5 seconds
2. anneal: 52° C. for 10 seconds
3. extension: 72° C. for 30 seconds (7.7 seconds/kb)
4. go to 1, 35 times
5. 4° C. until the PCR reaction is evaluated.
Total cycling time: 1 hour, 18 minutes, 30 seconds.

While the reaction is underway, thaw the PICOGREEN® reagent at room temperature.

Figure 7:
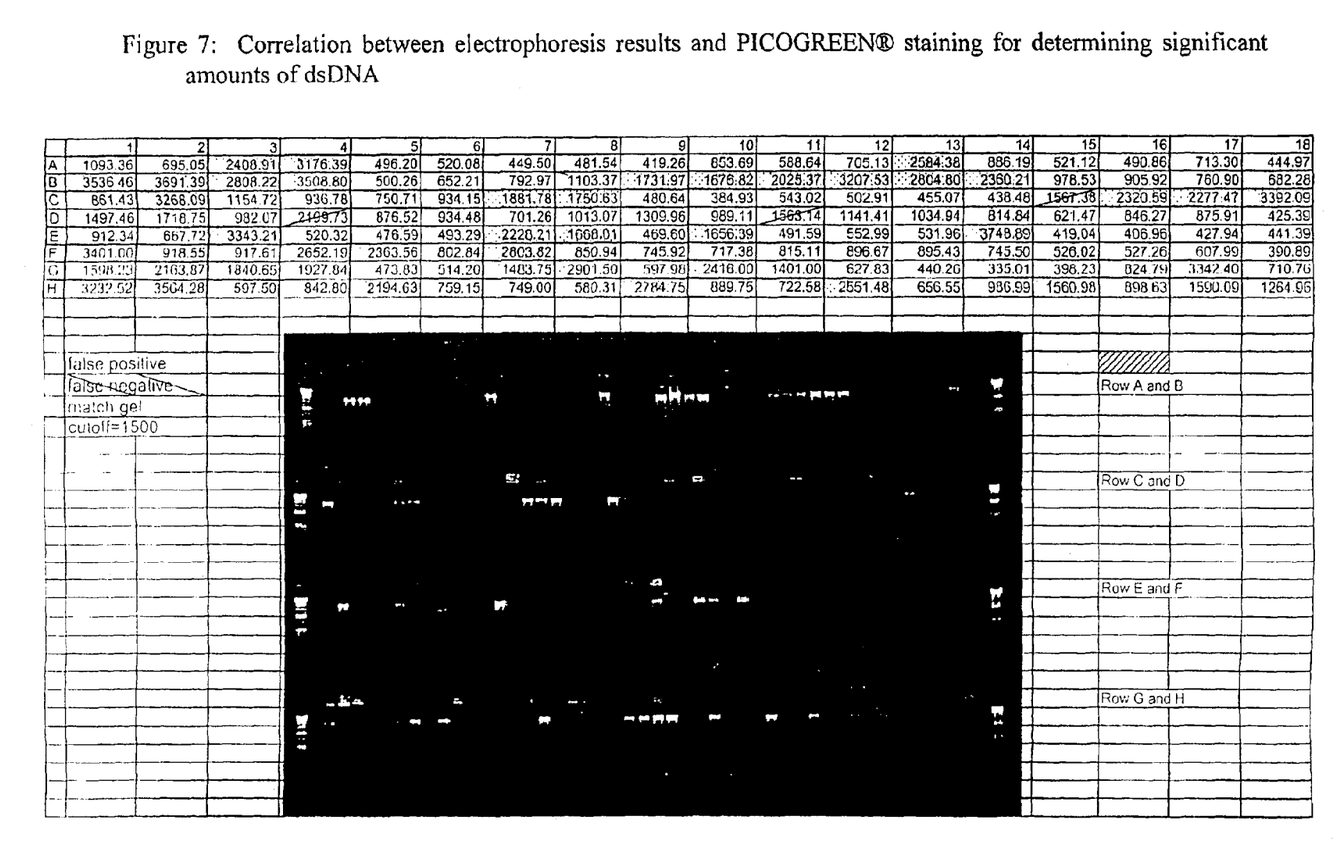
FIG. 7 is a picture of an electrophoresis gel stained to show the products of PCR reactions and a table of the PICOGREEN® results for the same PCR reactions.

Prepare a 1:150 dilution of PICOGREEN® in 1× TE Buffer. Prepare 10 mL per 384-well plate. Use the Robbins Hydra to aliquot 25 μL per well to an entire 384-well black plate. Use the Robbins Hydra to dispense 5 μL per well of the PCR reaction into the PICOGREEN® plate. Immediately place the plate into the fluorescence plate reader and mix by shaking for 10 seconds. Export the fluorescence signal data to a floppy disk. Import data into an Excel macro and generate a rearray list of positive clones using 1500 as the threshold. See FIG. 7 for an example of final PICOGREEN® data obtained from a PCR screen. Open the rearray list in the TECAN robot and rearray clones from the glycerol stock plate into a 96-well deep-well plate containing Superbroth and appropriate antibiotics. After the plates have been incubated, the cultures in them are sequenced in an automated process.

Example 3

Transposon Expedited Multiplex Sequencing of Unknown Sequences in Vector PCR4Blunt-TOPO Transposon Reaction The transposon reaction was performed using the Genome Priming System (GPS) kit from New England BioLabs. All of the components provided in the kit were used with the exception of the transposon GPS1. The transposon utilized was a modified version of GPS1. Two variations were generated. In one variant, pGPS-Apra, the existing resistance marker has been replaced by the apramycin resistant gene. This was performed to ensure that the vector could be used to sequence any vector regardless of resistance marker. In another variant, pGPS-Apra-Y2 um a "stuffer" region containing the yeast 2 um replication origin was cloned into the transposon thus increasing its size to 5 kb (FIG. 6). This alteration was created in order to improve the efficiency of the process by screening out transpositions into the vector backbone. The reaction was transformed by electroporation into DH10B *E. coli* competent cells and plated on Luria-Bertani (1.0% bacto-tryptone, 0.5% bacto-yeast extract, 1.0% NaCl, pH 7.0) agar plates containing the appropriate antibiotics (aprarnycin (100 μg/ml)/kanamycin (50 μg/ml)) for selection of clones harboring the transposon. The growth period is 20-22 hours.

TEMS (Transposon Expedited Multiplex Sequencing)

The size of all target DNA sequences subjected to TEMS was evaluated by restriction digest of the target DNA-containing vectors with NotI. Plasmid sets containing target DNA sequences of various sizes contained in the same vector backbone were pooled. Equimolar concentrations were calculated for each target DNA sequence prior to pooling. The transposon reaction was performed treating the pooled DNA template as a single template. For six-fold coverage of each base of each target DNA sequence, the total size of each target DNA sequence was multiplied by our standard factor of 18 clones per 1 kb of sequence to determine the number of randomly selected clones to sequence. Based on the total size of the vector and the total size of the target DNA sequence, a probability of the location of the transposon insertion was calculated. Multiplying this factor with the number of clones for six-fold coverage determines how many clones to randomly select and subject to the PCR screen.

The calculated number of colonies were selected and inoculated into Superbroth (bacto-tryptone, yeast extract, NaCl, NaOH) media containing the appropriate antibiotics on 96 or 384 well culture plates. These culture plates were grown overnight without shaking for 18-22 hours depending on the format of the growth plate (96/384 well). Glycerol stocks were made for temporary storage of the plate. 50% glycerol was added directly to the plate and mixed. This allowed indefinite storage in −80 C.

Screening out Vector Insertions by PCR

The primer sequence selected to amplify the vector portion of the clones for screening were the complement sequences of the universal primers M13F(−20) and M13R The sequence is as follows: 5'-ACTGGCCGTCGTTTTAC-3' (SEQ ID NO: 3) and 5'-CATGGTCATAGCTGTT-3' (SEQ ID NO: 4). Culture PCR was assembled with the following conditions: the template was deposited into the PCR reaction reagent preparation using a pin replicator tool which aliquoted approximately 1 μL. For the 96-well format, the 10 times PCR buffer composition was 100 mM Tris-HCl pH 8.3; 500 mM KCl: 15 mM MgC12; 0.01% w/v gelatin. Five picomoles of the forward primer and five pmoles of the reverse primer were used in each reaction. The dNTP concentration in the reaction was 2.5 mM final concentration. The quantity of Taq polymerase added to each reaction was 0.1 units. All reactions were carried out in a total volume of 50 μl. The 384-well format PCR was done in a total volume of 25 μl using the TaKaRa Z-Taq kit obtained from Panvera Corporation, 545 Science Drive, Madison, Wis. 53711. This kit consists of Z-taq polymerase (2.5 units/μL), 10× Z-Taq buffer containing a 30 mM concentration of Mg2+, and a JNTP mixture (2.5 mM each). Thermocyclers were run with a heated lid (MJ Research). This PCR cycle was designed to amplify only the vector without the transposon due to the short elongation time. Black PCR plates were used so that the fluorescent analysis could later be performed directly in the plates.

Analysis Conditions Using PICOGREEN®

Upon completion of the PCR, 25 ul of PICOGREEN® was added the PCR plate. A dilution of PICOGREEN® stock 1:200 in 1× TE (tris-acetate, EDTA) buffer at 50 ul volume was mixed with 10 ul of PCR reaction. The plate was read in a spectrofluorometer where the molecules are excited at 480 nm and the signal is emitted at 540 nm. The PCR products fluorescing above a predetermined threshold were the positive clones to be sequenced. The threshold was experimentally determined using known constructs containing the transposon either in the vector or in an insert to the vector. The positive clones were sorted and compressed into a format suitable for array by the TECAN robotic arm. Glycerol stocks were inoculated into the 96 deep well plate containing 1.5 ml of Superbroth (bacto-tryptone, yeast extract, NaCl, 5N NaOH) and appropriate antibiotics. These cultures were grown for a 24 hour time period and then the DNA targets from the cultures are sequenced using the primers at either end of the transposon.

Sequence Assembly

After vector trimming and base calling of the raw sequences using Phred software, the sequences are assembled using Phrap software (see Brent Ewing, LaDeana Hillier, Michael C. Wendl, and Phil Green. Base-calling of automated sequencer traces using phred. I. Accuracy assessment. 1998. Genome Research 8:175-185. and Brent Ewing and Phil Green Base-calling of automated sequencer traces using phred. II. Error probabilities. 1998. Genome Research 8:186-194). The assembly is reviewed using consed software. (See Consed: A Graphical Tool for Sequence Finishing Gordon et al 1998.) Criteria for completion are high quality, six-fold coverage of the entire full-length gene. The expected error rate per 10 kb of sequence should be<0.1. If these criteria are not met, primers are selected along with templates for primer walking sequencing of the error-prone section of target DNA sequence. The primer walking sequencing is done on either the ABI 310 sequencer or through high-throughput sequencing using the ABI 3700 depending on volume of sequencing needed, and those sequences are subsequently added to the assembly. BLAST analysis is done for comparison especially to known genes. (See: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402; and Zhang, J. & Madden, T. L. (1997) "PowerBLAST: A new network BLAST application for interactive or automated sequence analysis and annotation." Genome Res. 7:649-656.) The generated full-length sequence is imported into another assembly program called Sequencher. (See Cash, H., Clark, B., Galt, J., Garb, C., Goebel III, C. J., & Singer, J. *Sequencher User Guide "The complete Software Solution for Sequencing DNA"*. Gene Codes Corporation. 1999.) With this program, it is easy to view the open reading frame to be sure mutations, if any, have not caused a frame shift.

It is to be understood that the foregoing examples are exemplary and explanatory only and are not restrictive of the invention. Various changes may be made to the embodiments described above by one of skill in the art without departing from the scope of the invention, as defined by the following claims.

The invention claimed is:

1. A process for parallel, transposon-mediated sequencing of DNA, the process comprising:
   i) providing one or more target DNA sequences, each inserted into a vector at an insertion site;
   ii) amplifying each target DNA-containing vector and pooling them, wherein each target DNA sequence is represented in the pool in an substantially equal amount per kb;
   iii) exposing the pool of target DNA-containing vectors to a selectable transposon, wherein the selectable transposon integrates into the target DNA-containing vectors at substantially random sites to form a pool of target DNA- and transposon-containing vectors;
   iv) transforming cells with the pool of target DNA- and transposon-containing vectors and isolating and growing a representative number of individual transformants into cultures under selection conditions;
   v) performing a polymerase chain reaction on DNA from each culture, wherein the polymerase chain reaction uses primers complementary to the 3' ends of the vector sequence at the insertion site and has an extension time during each reaction cycle of the polymerase chain reaction sufficient to efficiently produce a DNA with the size of a full-length of the vector sequence but too short to efficiently produce a DNA with the size of a full-length of the vector sequence plus the transposon sequence;
   vi) measuring the amount of DNA produced in each polymerase chain reaction;
   vii) selecting cultures whose polymerase chain reactions produced substantial amounts of DNA above a cutoff value; and
   viii) sequencing the transposon flanking regions of the target DNA-containing vector from the selected cultures.

2. The process of claim 1, wherein one or more of steps i) to viii) are automated.

3. The process of claim 1, wherein the step of measuring the amount of DNA produced in each polymerase chain reaction comprises adding a fluorescent stain selective for dsDNA to the finished polymerase chain reaction and measuring the resulting amount of fluorescence.

4. The process of claim 3, wherein one or more of steps i) to viii) are automated.

5. The process of claim 3, wherein the fluorescent stain selective for dsDNA is selected from the group consisting of PICOGREEN® and bisbenzimide dyes.

6. The process of claim 3, wherein the fluorescent stain selective for dsDNA is PICOGREEN®.

7. The process of claim 1, wherein the vector and transposon carry different selectable markers.

8. The process of claim 1, wherein the transposon is at least 3 kb.

9. The process of claim 8, wherein the transposon is at least 4 kb.

10. The process of claim 9, wherein the transposon is GPS-Apra-2 um-URA3.

11. The process of claim 8, wherein the transposon is at least 5 kb.

12. The process of claim 1, wherein the transposon is equal to or greater than the vector in length.

13. The process of claim 12, wherein the transposon is at least about 5/4 the length of the vector.

14. The process of claim 13, wherein the transposon is about 5 kb and the vector is about 4 kb.

15. The process of claim 12, wherein the transposon is at least about 5/3 the length of the vector.

16. The process of claim 15, wherein the transposon is about 5 kb and the vector is about 3 kb.

* * * * *

SEQUENCE LISTING

<160> NUMBER OF SEQ ID NOS: 4

<210> SEQ ID NO 1
<211> LENGTH: 2613

<212> TYPE: DNA
<213> ORGANISM: Artificial
<220> FEATURE:
<223> OTHER INFORMATION: GPS-Apra transposon vector

<400> SEQUENCE: 1

```
ggtaccctgt gaatgcgcaa accaacccct ggcagaacat atccatcgcg tccgccatct      60
ccagcagccg cacgcggcgc atctcgggca gcgttgggtc ctggccacgg gtgcgcatga     120
tcgtgctcct gtcgttgagg acccggctag gctggcgggg ttgccttact ggttagcaga     180
atgaatcacc gatacgcgag cgaacgtgaa gcgactgctg ctgcaaaacg tctgcgacct     240
gagcaacaac atgaatggtc ttcggtttcc gtgtttcgta aagtctggaa acgcggaagt     300
cagcgccctg caccattatg ttccggatct atgtcgggtg cggagaaaga ggtaatgaaa     360
tggcagatcc ctggcttgtt gtccacaacc gttaaacctt aaaagcttta aaagccttat     420
atattctttt ttttcttata aaacttaaaa ccttagaggc tatttaagtt gctgatttat     480
attaatttta ttgttcaaac atgagagctt agtacgtgaa acatgagagc ttagtacgtt     540
agccatgaga gcttagtacg ttagccatga gggtttagtt cgttaaacat gagagcttag     600
tacgttaaac atgagactta gtacgtgaaa catgagagct tagtacgtac tatcaacagg     660
ttgaactgct gatcttcgga tctatgtcgg gtgcggagaa agaggtaatg aaatggcatc     720
cggatctgca tcgcaggatg ctgctggcta ccctgtggaa cacctacatc tgtattaacg     780
aagcgctggc attgaccctg agtgattttt ctctggtccc gccgcatcca taccgccagt     840
tgtttaccct cacaacgttc cagtaaccgg gcatgttcat catcagtaac ccgtatcgtg     900
agcatcctct ctcgtttcat cggtatcatt accccccatga acagaaatcc cccttacacg     960
gaggcatcag tgaccaaaca ggaaaaaacc gcccttaaca tggcccgctt tatcagaagc    1020
cagacattaa cgcttctgga gaaactcaac gagctggacg cggatgaaca ggcagagctc    1080
ttactgtcat gccatccgta tgtgggcgga caataaagtc ttaaactgaa caaaatagat    1140
ctaaactatg acaataaagt cttaaactag acagaatagt tgtaaactga aatcagtcca    1200
gttatgctgt gaaaaagcat actggacttt tgttatggct aaagcaaact cttcattttc    1260
tgaagtgcaa attgcccgtc gtattaaaga ggggcgtggg gtcgacgcgg ccgcgccgta    1320
tttgcagtac cagcgtacgg cccacagaat gatgtcacgc tgaaaatgcc ggcctttgaa    1380
tgggttcatg tgcagctcca tcagcaaaag gggatgataa gtttatcacc accgactatt    1440
tgcaacagtg ccgttgatcg tgctatgatc gactgatgtc atcagcggtg gagtgcaatg    1500
tcgtgcaata cgaatggcga aaagccgagc tcatcggtca gcttctcaac cttggggtta    1560
cccccggcgg tgtgctgctg gtccacagct ccttccgtag cgtccggccc ctcgaagatg    1620
ggccacttgg actgatcgag gccctgcgtg ctgcgctggg tccgggaggg acgctcgtca    1680
tgccctcgtg gtcaggtctg gacgacgagc cgttcgatcc tgccacgtcg cccgttacac    1740
cggaccttgg agttgtctct gacacattct ggcgcctgcc aaatgtaaag cgcagcgccc    1800
atccatttgc ctttgcggca gcggggccac aggcagagca gatcatctct gatccattgc    1860
ccctgccacc tcactcgcct gcaagcccgg tcgcccgtgt ccatgaactc gatgggcagg    1920
tacttctcct cggcgtggga cacgatgcca acacgacgct gcatcttgcc gagttgatgg    1980
caaaggttcc ctatggggtg ccgagacact gcaccattct tcaggatggc aagttggtac    2040
gcgtcgatta tctcgagaat gaccactgct gtgagcgctt tgccttggcg gacaggtggc    2100
tcaaggagaa gagccttcag aaggaaggtc cagtcggtca tgcctttgct cggttgatcc    2160
```

```
gctcccgcga cattgtggcg acagccctgg gtcaactggg ccgagatccg ttgatcttcc    2220
tgcatccgcc agagggcggg atgcgaagaa tgcgatgccg ctcgccagtc gattggctga    2280
gctcatgagc ggagaacgag atgacgttgg aggggcaagg tcgcgctgat tgctggggca    2340
acacgtggag cggatcgggg attgtctttc ttcagctcgc tgatgatatg ctgacgctca    2400
atgccgtttg gactagtgtc gaccaaccag ataagtgaaa tctagttcca aactattttg    2460
tcatttttaa ttttcgtatt agcttacgac gctacaccca gttcccatct attttgtcac    2520
tcttccctaa ataatcctta aaaactccat ttccacccct cccagttccc aactattttg    2580
tccgcccaca ccgtaagatg cttttctgtg act                                 2613

<210> SEQ ID NO 2
<211> LENGTH: 6114
<212> TYPE: DNA
<213> ORGANISM: Artificial
<220> FEATURE:
<223> OTHER INFORMATION: GPS-Apra-2um-URA3 transposon vector

<400> SEQUENCE: 2
ggtaccctgt gaatgcgcaa accaaccctt ggcagaacat atccatcgcg tccgccatct      60
ccagcagccg cacgcggcgc atctcgggca gcgttgggtc ctggccacgg gtgcgcatga     120
tcgtgctcct gtcgttgagg acccggctag gctggcgggg ttgccttact ggttagcaga     180
atgaatcacc gatacgcgag cgaacgtgaa gcgactgctg ctgcaaaacg tctgcgacct     240
gagcaacaac atgaatggtc ttcggtttcc gtgtttcgta aagtctggaa acgcggaagt     300
cagcgccctg caccattatg ttccggatct atgtcgggtg cggagaaaga ggtaatgaaa     360
tggcagatcc ctggcttgtt gtccacaacc gttaaacctt aaaagcttta aagccttat     420 atattctttt ttttcttata aaacttaaaa ccttagaggc tatttaagtt gctgatttat     480 attaattta ttgttcaaac atgagagctt agtacgtgaa acatgagagc ttagtacgtt     540
agccatgaga gcttagtacg ttagccatga gggtttagtt cgttaaacat gagagcttag     600
tacgttaaac atgagagctt agtacgtgaa acatgagagc ttagtacgta ctatcaacag     660
gttgaactgc tgatcttcgg atctatgtcg ggtgcggaga agaggtaat gaaatggcat     720 ccggatctgc atcgcaggat gctgctggct accctgtgga acacctacat ctgtattaac     780
gaagcgctgg cattgaccct gagtgatttt tctctggtcc cgccgcatcc ataccgccag     840
ttgtttaccc tcacaacgtt ccagtaaccg gcatgttca tcatcagtaa cccgtatcgt     900
gagcatcctc tctcgtttca tcggtatcat taccccatg aacagaaatc ccccttacac     960
ggaggcatca gtgaccaaac aggaaaaaac cgcccttaac atggcccgct ttatcagaag    1020
ccagacatta acgcttctgg agaaactcaa cgagctggac gcggatgaac aggcagagct    1080
cttactgtca tgccatccgt atgtgggcgg acaataaagt cttaaactga acaaaataga    1140
tctaaactat gacaataaag tcttaaacta gacagaatag ttgtaaactg aaatcagtcc    1200
agttatgctg tgaaaagca tactggactt tgttatggc taaagcaaac tcttcatttt    1260
ctgaagtgca aattgcccgt cgtattaaag agggggcgtgg ggtcgacgcg ccgcgaatt    1320 ctgaaccagt cctaaaacga gtaaataga ccggcaattc ttcaagcaat aaacaggaat    1380
accaattatt aaaagataac ttagtcagat cgtacaataa gctttgaag aaaaatgcgc    1440 cttattcaat ctttgctata aaaaatggcc caaaatctca cattggaaga catttgatga    1500
cctcatttct ttcaatgaag ggcctaacgg agttgactaa tgttgtggga aattggagcg    1560
ataagcgtgc ttctgccgtg gccaggacaa cgtatactca tcagataaca gcaataccctg    1620
```

```
atcactactt cgcactagtt tctcggtact atgcatatga tccaatatca aaggaaatga    1680
tagcattgaa ggatgagact aatccaattg aggagtggca gcatatagaa cagctaaagg    1740
gtagtgctga aggaagcata cgatacccg catggaatgg gataatatca caggaggtac     1800
tagactacct ttcatcctac ataaatagac gcatataagt acgcatttaa gcataaacac    1860
gcactatgcc gttcttctca tgtatatata tatacaggca acacgcagat ataggtgcga    1920
cgtgaacagt gagctgtatg tgcgcagctc gcgttgcatt ttcggaagcg ctcgttttcg    1980
gaaacgcttt gaagttccta ttccgaagtt cctattctct agaaagtata ggaacttcag    2040
agcgcttttg aaaccaaaa gcgctctgaa gacgcacttt caaaaaacca aaacgcacc      2100 ggactgtaac gagctactaa aatattgcga ataccgcttc cacaaacatt gctcaaaagt    2160
atctctttgc tatatatctc tgtgctatat ccctatataa cctacccatc cacctttcgc    2220
tccttgaact tgcatctaaa ctcgacctct acatttttta tgtttatctc tagtattact    2280
ctttagacaa aaaaattgta gtaagaacta ttcatagagt gaatcgaaaa caatacgaaa    2340
atgtaaacat ttcctatacg tagtatatag agacaaaata aagaaaccg ttcataattt     2400 tctgaccaat gaagaatcat caacgctatc actttctgtt cacaaagtat gcgcaatcca    2460
catcggtata gaatataatc ggggatgcct ttatcttgaa aaatgcacc cgcagcttcg     2520 ctagtaatca gtaaacgcgg gaagtggagt caggcttttt ttatggaaga gaaaatagac    2580
accaaagtag ccttcttcta accttaacgg acctacagtg caaaaagtta tcaagagact    2640
gcattataga gcgcacaaag gagaaaaaaa gtaatcaag atgctttgtt agaaaatag      2700 cgctctcggg atgcattttt gtagaacaaa aaagaagtat agattctttg ttggtaaaat    2760
agcgctctcg cgttgcattt ctgttctgta aaatgcagc tcagattctt tgtttgaaaa    2820
attagcgctc tcgcgttgca ttttgtttt acaaaaatga agcacagatt cttcgttggt     2880
aaaatagcgc tttcgcgttg catttctgtt ctgtaaaaat gcagctcaga ttcttgttt    2940 gaaaaattag cgctctcgcg ttgcattttt gttctacaaa atgaagcaca gatgcttcgt    3000
taacaaagat atgctattga agtgcaagat ggaaacgcag aaaatgaacc ggggatgcga    3060
cgtgcaagat tacctatgca atagatgcaa tagtttctcc aggaaccgaa atacatacat    3120
tgtcttccgt aaagcgctag actatatatt attatacagg ttcaaatata ctatctgttt    3180
cagggaaaac tcccaggttc ggatgttcaa aattcaatga tgggtaacaa gtacgatcgt    3240
aaatctgtaa aacagtttgt cggatattag gctgtatctc ctcaaagcgt attcgaatat    3300
cattgagaag ctgcagcgtc acatcggata ataatgatgg cagccattgt agaagtgcct    3360
tttgcatttc tagtctcttt ctcggtctag ctagttttac tacatcgcga agatagaatc    3420
ttagatcaca ctgcctttgc tgagctggat caatagagta acaaaagagt ggtaaggcct    3480
cgttaaagga caaggacctg agcggaagtg tatcgtacag tagacggagt atactagtat    3540
agtctatagt ccgtggaatt ctcatgtttg acagcttatc atcgataagc ttttcaattc    3600
aattcatcat ttttttttta ttcttttttt tgatttcggt ttctttgaaa ttttttttgat   3660 tcggtaatct ccgaacagaa ggaagaacga aggaaggagc acagacttag attggtatat    3720
atacgcatat gtagtgttga agaaacatga aattgcccag tattckyrrc cgcwwytgca    3780
cagaacaaaa acctgcagga aacgaagata aatcatgtcg aaagctacat ataaggaacg    3840
tgctgctact catcctagtc ctgttgctgc caagctattt aatatcatgc acgaaaagca    3900
aacaaacttg tgtgcttcat tggatgttcg taccaccaag gaattactgg agttagttga    3960
```

-continued

```
agcattaggt cccaaaattt gtttactaaa aacacatgtg gatatcttga ctgattttc    4020
catggagggc acagttaagc cgctaaaggc attatccgcc aagtacaatt ttttactctt    4080
cgaagacaga aaatttgctg acattggtaa tacagtcaaa ttgcagtact ctgcgggtgt    4140
atacagaata gcagaatggg cagacattac gaatgcacac ggtgtggtgg gcccaggtat    4200
tgttagcggt ttgaagcagg cggcagaaga agtaacaaag gaacctagag gccttttgat    4260
gttagcagaa ttgtcatgca agggctccct atctactgga gaatatacta agggtactgt    4320
tgacattgcg aagagcgaca aagattttgt tatcggcttt attgctcaaa gagacatggg    4380
tggaagagat gaaggttacg attggttgat tatgacaccc ggtgtgggtt tagatgacaa    4440
gggagacgca ttgggtcaac agtatagaac cgtggatgat gtggtctcta caggatctga    4500
cattattatt gttggaagag gactatttgc aaagggaagg gatgctaagg tagagggtga    4560
acgttacaga aaagcaggct gggaagcata tttgagaaga tgcggccagc aaaactaaaa    4620
aactgtatta taagtaaatg catgtatact aaactcacaa attagagctt caatttaatt    4680
atatcagtta ttacccggga atctcggtcg taatgatttt tataatgacg aaaaaaaaaa    4740
aattggaaag aaaaagcttt aatgcggtag tttatcacag ttaaattgct aacgcagtca    4800
ggcaccggcg gccgcgccgt atttgcagta ccagcgtacg gcccacagaa tgatgtcacg    4860
ctgaaaatgc cggcctttga atgggttcat gtgcagctcc atcagcaaaa ggggatgata    4920
agtttatcac caccgactat ttgcaacagt gccgttgatc gtgctatgat cgactgatgt    4980
catcagcggt ggagtgcaat gtcgtgcaat acgaatggcg aaaagccgag ctcatcggtc    5040
agcttctcaa ccttggggtt accccggcg gtgtgctgct ggtccacagc tccttccgta    5100
gcgtccggcc cctcgaagat gggccacttg gactgatcga ggccctgcgt gctgcgctgg    5160
gtccgggagg gacgctcgtc atgccctcgt ggtcaggtct ggacgacgag ccgttcgatc    5220
ctgccacgtc gcccgttaca ccggaccttg gagttgtctc tgacacattc tggcgcctgc    5280
caaatgtaaa gcgcagcgcc catccatttg cctttgcggc agcggggcca caggcagagc    5340
agatcatctc tgatccattg cccctgccac ctcactcgcc tgcaagcccg gtcgcccgtg    5400
tccatgaact cgatgggcag gtacttctcc tcggcgtggg acacgatgcc aacacgacgc    5460
tgcatcttgc cgagttgatg gcaaaggttc cctatgggt gccgagacac tgcaccattc    5520
ttcaggatgg caagttggta cgcgtcgatt atctcgagaa tgaccactgc tgtgagcgct    5580
ttgccttggc ggacaggtgg ctcaaggaga agagccttca gaaggaaggt ccagtcggtc    5640
atgcctttgc tcggttgatc cgctcccgcg acattgtggc gacagccctg ggtcaactgg    5700
gccgagatcc gttgatcttc ctgcatccgc cagagggcgg gatgcgaaga atgcgatgcc    5760
gctcgccagt cgattggctg agctcatgag cggagaacga gatgacgttg gaggggcaag    5820
gtcgcgctga ttgctgggc aacacgtgga gcggatcggg gattgtcttt cttcagctcg    5880
ctgatgatat gctgacgctc aatgccgttt ggactagtgt cgaccaacca gataagtgaa    5940
atctagttcc aaactatttt gtcattttta atttcgtat tagcttacga cgctacaccc    6000
agttcccatc tattttgtca ctcttcccta ataatccttt aaaaactcca tttccacccc    6060
tcccagttcc caactatttt gtccgcccac accgtaagat gcttttctgt gact          6114
```

<210> SEQ ID NO 3
<211> LENGTH: 16
<212> TYPE: DNA
<213> ORGANISM: Artificial
<220> FEATURE:
<223> OTHER INFORMATION: primer

```
<400> SEQUENCE: 3
actggccgtc gtttta                                                    16

<210> SEQ ID NO 4
<211> LENGTH: 16
<212> TYPE: DNA
<213> ORGANISM: Artificial
<220> FEATURE:
<223> OTHER INFORMATION: primer

<400> SEQUENCE: 4
catggtcata gctgtt                                                    16
```